US012285337B2

(12) United States Patent
Rabito et al.

(10) Patent No.: US 12,285,337 B2
(45) Date of Patent: *Apr. 29, 2025

(54) SPRING AND COIL DEVICES FOR PAPILLARY MUSCLE APPROXIMATION AND VENTRICLE REMODELING

(71) Applicant: Edwards Lifesciences Corporation, Irvine, CA (US)

(72) Inventors: Glen T. Rabito, Lake Forest, CA (US); Robert C. Taft, Orange, CA (US); Alison S. Curtis, Colden, CO (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 310 days.

This patent is subject to a terminal disclaimer.

(21) Appl. No.: 17/861,017

(22) Filed: Jul. 8, 2022

(65) Prior Publication Data

US 2022/0338991 A1    Oct. 27, 2022

Related U.S. Application Data

(62) Division of application No. 16/549,056, filed on Aug. 23, 2019, now Pat. No. 11,413,146.
(Continued)

(51) Int. Cl.
*A61F 2/24* (2006.01)
*A61B 17/04* (2006.01)
*A61B 17/06* (2006.01)

(52) U.S. Cl.
CPC ...... *A61F 2/2466* (2013.01); *A61B 17/06004* (2013.01); *A61F 2/2454* (2013.01); *A61F 2/246* (2013.01); *A61B 2017/0498* (2013.01); *A61B 2017/06076* (2013.01); *A61F 2230/0091* (2013.01)

(58) Field of Classification Search
CPC ............ A61B 17/0401; A61B 17/0469; A61B 17/0487; A61B 17/06004; A61B 17/083; A61B 2017/00243; A61B 2017/0409; A61B 2017/0414; A61B 2017/0441; A61B 2017/0443; A61B 2017/0464; A61B 2017/0496; A61B 2017/0498; A61B 2017/06076; A61F 2/2427; A61F 2/2454;
(Continued)

(56) References Cited

U.S. PATENT DOCUMENTS 8,043,368 B2   10/2011   Crabtree
8,206,439 B2    6/2012   Gomez Duran
(Continued)

FOREIGN PATENT DOCUMENTS

WO    2011034973 A2    3/2011

OTHER PUBLICATIONS

Hvass et al., "The Papillary Muscle Sling for Ischemic Mitral Regurgitation." J Thorac Cardiovasc Surg. Feb. 2010;139 (2):418-23.

*Primary Examiner* — Robert A Lynch
(74) *Attorney, Agent, or Firm* — CHANG & HALE LLP

(57) ABSTRACT

A method for treating a heart valve involves delivering a catheter into a ventricle of a heart, advancing a coil from the catheter, rotating the coil at least partially around a papillary muscle of the ventricle, embedding a distal end of the coil in tissue of the ventricle, and manipulating a suture coupled to the coil to adjust a position of the papillary muscle.

19 Claims, 10 Drawing Sheets

Related U.S. Application Data

(60) Provisional application No. 62/740,544, filed on Oct. 3, 2018.

(58) Field of Classification Search
CPC ...... A61F 2/2457; A61F 2/246; A61F 2/2466; A61F 2230/0091
See application file for complete search history.

(56) References Cited

U.S. PATENT DOCUMENTS

| | | |
|---|---|---|
| 8,382,653 B2 | 2/2013 | Dubi et al. |
| 8,523,755 B2 | 9/2013 | Almog et al. |
| 8,790,394 B2 | 7/2014 | Miller et al. |
| 9,237,886 B2 | 1/2016 | Seguin et al. |
| 9,364,326 B2 | 6/2016 | Yaron |
| 9,656,009 B2 | 5/2017 | Kheradvar et al. |
| 9,700,412 B2 | 7/2017 | Yaron et al. |
| 10,058,428 B1 | 8/2018 | Neustadter |
| 11,413,147 B2 * | 8/2022 | Oba ...................... A61F 2/2454 |
| 2006/0167474 A1 | 7/2006 | Bloom et al. |
| 2007/0255396 A1 | 11/2007 | Douk et al. |
| 2009/0222081 A1 | 9/2009 | Linder et al. |
| 2010/0185278 A1 | 7/2010 | Schankereli |
| 2011/0066233 A1 | 3/2011 | Thornton et al. |
| 2016/0220371 A1 | 8/2016 | Keane |

* cited by examiner ered as limiting the scope of the inventions. In addition, various features of different disclosed embodiments
SPRING AND COIL DEVICES FOR PAPILLARY MUSCLE APPROXIMATION AND VENTRICLE REMODELING

RELATED APPLICATION

This application is a divisional application of U.S. Utility patent application Ser. No. 16/549,056, filed Aug. 23, 2019 and entitled SPRING AND COIL DEVICES FOR PAPILLARY MUSCLE APPROXIMATION AND VENTRICLE REMODELING, which claims priority based on U.S. Provisional Patent Application Ser. No. 62/740,544, filed Oct. 3, 2018 and entitled SPRING AND COIL DEVICES FOR PAPILLARY MUSCLE APPROXIMATION AND VENTRICLE REMODELING, the complete disclosures of both of which are hereby incorporated herein by reference in their entireties.

BACKGROUND

Field

The present disclosure generally relates to the field of valve correction.

Description of Related Art

Heart valve dysfunction can result in regurgitation and other complications due to valve prolapse from failure of valve leaflets to properly coapt. For atrioventricular valves, papillary muscle position can affect the ability of valve leaflets to function properly.

SUMMARY

In some implementations, the present disclosure relates to a method for treating a heart valve. The method involves delivering a catheter into a ventricle of a heart, advancing a coil from the catheter, rotating the coil at least partially around a papillary muscle of the ventricle, embedding a distal end of the coil in tissue of the ventricle, and manipulating a suture coupled to the coil to adjust a position of the papillary muscle. Performing the method can improve at least one of prolapse of a heart valve associated with the ventricle and regurgitation of the heart valve. The distal end of the coil may comprise a pointed tip. In certain embodiments, the suture is contained at least partially within the coil and extends out from a proximal end on the coil. The method may further comprise drawing an end portion of the suture from the distal end of the coil, and coupling the end portion of the suture to a suture portion associated with another coil implanted in the ventricle.

In some implementations, the present disclosure relates to a method for treating a heart valve comprising introducing a coil to a ventricle of a heart, wrapping the coil along an inner wall of the ventricle, and capturing papillary muscles of the ventricle within the coil to thereby draw the papillary muscles together. In certain embodiments, the coil comprises an outer sleeve and a spring element disposed at least partially within the outer sleeve. For example, the outer sleeve can comprise one or more tissue anchor features. The outer sleeve may comprise material that promotes ingrowth with tissue of the inner wall of the ventricle. In certain embodiments, the spring element is configured to slide within the outer sleeve to accommodate contraction and expansion of the ventricle. The method may further comprise securing one or more of the outer sleeve and the spring element to an apex region of the ventricle. In certain embodiments, the spring element is fixed to the outer sleeve at one or more locations. In certain embodiments, the method further comprises securing the coil in an expanded state using one or more biodegradable elements, and allowing the biodegradable elements to degrade to thereby cause the coil to assume a contracted state.

In some implementations, the present disclosure relates to a method of reshaping a ventricle of a heart. The method comprises twisting an apex portion of a heart to at least partially constrict a ventricle of the heart and securing a clip device to the apex portion of the heart, thereby at least partially restricting dilation of a ventricle of the heart. In certain embodiments, securing the clip device to the apex portion of the heart involves engaging the clip device with pericardial tissue associated with the apex portion of the heart.

In some implementations, the present disclosure relates to a method of approximating papillary muscles. The method comprises introducing a spiral form into a ventricle of a heart, the spiral form having an inner end portion and an outer end portion, wrapping the outer end portion around a first papillary muscle, wrapping the outer end portion around a second papillary muscle, and rotating the spiral form to draw the first and second papillary muscles inward. The spiral form can be generally flat. In certain embodiments, the spiral form is at least partially conical in shape. The method may further comprise passing a guide wire around the first papillary muscle and the second papillary muscle, wherein said wrapping the outer end portion around the first papillary muscle and the second papillary muscle is performed using the guide wire.

In some implementations, the present disclosure relates to a papillary muscle manipulation device comprising a coil portion, a first arm portion configured to wrap at least partially around a first papillary muscle of a heart, and a second arm portion configured to wrap at least partially around a second papillary muscle of the heart. The coil portion is configured to exert force of the first arm portion and the second arm portion to draw the first papillary muscle and the second papillary muscle together. In certain embodiments, the second arm portion, and the coil portion are separate attachable components. The papillary muscle manipulation device can be configured to be compressed to fit within a catheter. The first arm portion may comprise a tissue anchor configured to embed in tissue of the first papillary muscle.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

DETAILED DESCRIPTION

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

In humans and other vertebrate animals, the heart generally comprises a muscular organ having four pumping chambers, wherein the flow thereof is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.).

Figure 1:
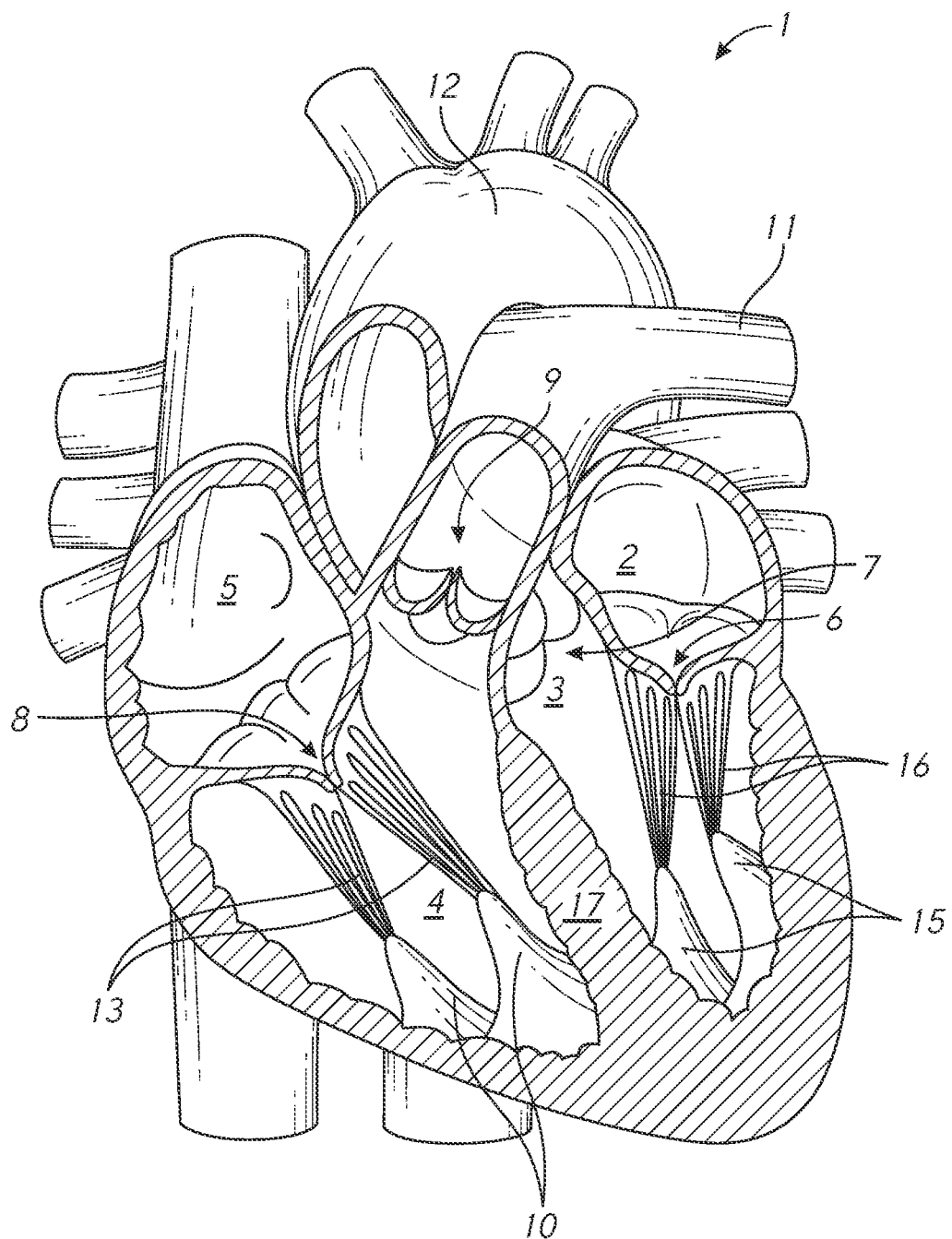
FIG. 1 provides a cross-sectional view of a human heart.

FIG. 1 illustrates an example representation of a heart 1 having various features relevant to certain embodiments of the present disclosure. The heart 1 includes four chambers, namely the left atrium 2, the left ventricle 3, the right ventricle 4, and the right atrium 5. A wall of muscle 17, referred to as the septum, separates the left 2 and right 5 atria and the left 3 and right 4 ventricles. The heart 1 further includes four valves for aiding the circulation of blood therein, including the tricuspid valve 8, which separates the right atrium 5 from the right ventricle 4. The tricuspid valve 8 may generally have three cusps or leaflets and may generally close during ventricular contraction (i.e., systole) and open during ventricular expansion (i.e., diastole). The valves of the heart 1 further include the pulmonary valve 9, which separates the right ventricle 4 from the pulmonary artery 11, and may be configured to open during systole so that blood may be pumped toward the lungs, and close during diastole to prevent blood from leaking back into the heart from the pulmonary artery. The pulmonary valve 9 generally has three cusps/leaflets, wherein each one may have a crescent-type shape. The heart 1 further includes the mitral valve 6, which generally has two cusps/leaflets and separates the left atrium 2 from the left ventricle 3. The mitral valve 6 may generally be configured to open during diastole so that blood in the left atrium 2 can flow into the left ventricle 3, and advantageously close during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

Heart valves may generally comprise a relatively dense fibrous ring, referred to herein as the annulus, as well as a plurality of leaflets or cusps attached to the annulus. Generally, the size of the leaflets or cusps may be such that when the heart contracts the resulting increased blood pressure produced within the corresponding heart chamber forces the leaflets at least partially open to allow flow from the heart chamber. As the pressure in the heart chamber subsides, the pressure in the subsequent chamber or blood vessel may become dominant and press back against the leaflets. As a result, the leaflets/cusps come in apposition to each other, thereby closing the flow passage.

The atrioventricular (i.e., mitral and tricuspid) heart valves may further comprise a collection of chordae tendineae and papillary muscles for securing the leaflets of the respective valves to promote and/or facilitate proper coaptation of the valve leaflets and prevent prolapse thereof. The papillary muscles, for example, may generally comprise finger-like projections from the ventricle wall. With respect to the tricuspid valve 8, the normal tricuspid valve may comprise three leaflets (two shown in FIG. 1) and three corresponding papillary muscles 10 (two shown in FIG. 1). The leaflets of the tricuspid valve may be referred to as the anterior, posterior and septal leaflets, respectively. The valve leaflets are connected to the papillary muscles by the chordae tendineae 13, which are disposed in the right ventricle 4 along with the papillary muscles 10. Although tricuspid valves are described herein as comprising three leaflets, it should be understood that tricuspid valves may occur with two or four leaflets in certain patients and/or conditions; the principles relating to papillary muscle adjustment disclosed herein are applicable to atrioventricular valves having any number of leaflets and/or papillary muscles associated therewith.

The right ventricular papillary muscles 10 originate in the right ventricle wall, and attach to the anterior, posterior and septal leaflets of the tricuspid valve, respectively, via the chordae tendineae 13. The papillary muscles 10 of the right ventricle 4 may have variable anatomy; the anterior papillary may generally be the most prominent of the papillary muscles. The papillary muscles 10 may serve to secure the leaflets of the tricuspid valve 8 to prevent prolapsing of the leaflets into the right atrium 5 during ventricular systole. Tricuspid regurgitation can be the result of papillary dysfunction or chordae rupture.

With respect to the mitral valve 6, a normal mitral valve may comprise two leaflets (anterior and posterior) and two corresponding papillary muscles 15. The papillary muscles 15 originate in the left ventricle wall and project into the left ventricle 3. Generally, the anterior leaflet may cover approximately two-thirds of the valve annulus. Although the anterior leaflet covers a greater portion of the annulus, the posterior leaflet may comprise a larger surface area in certain anatomies.

The valve leaflets of the mitral valve 6 may be prevented from prolapsing into the left atrium 2 by the action of the chordae tendineae 16 tendons connecting the valve leaflets to the papillary muscles 15. The relatively inelastic chordae tendineae 16 are attached at one end to the papillary muscles 15 and at the other to the valve leaflets; chordae tendineae from each of the papillary muscles 15 are attached to a respective leaflet of the mitral valve 6. Thus, when the left ventricle 3 contracts, the intraventricular pressure forces the valve to close, while the chordae tendineae 16 keep the leaflets coapting together and prevent the valve from opening in the wrong direction, thereby preventing blood to flow back to the left atrium 2. The various chords of the chordae tendineae may have different thicknesses, wherein relatively thinner chords are attached to the free leaflet margin, while relatively thicker chords (e.g., strut chords) are attached farther away from the free margin.

The present disclosure provides systems devices and methods for implementing percutaneous papillary muscle approximation and/or ventricular reshaping, which may be used or implemented for the purpose of treating functional mitral regurgitation (FMR), and/or other cardiac defect or condition. In some implementations, papillary muscle approximation in accordance with the present disclosure utilizes one or more coil and/or spring devices, as described in detail below.

Generally, functional mitral regurgitation (FMR) may be considered a disease or condition of the left ventricle of the heart. Functional mitral regurgitation may be developed, for example, after or in connection with myocardial infarction or coronary artery disease. In connection with various heart conditions, as a portion of the heart loses blood supply, one or more ventricles of the heart, such as the left ventricle, may dilate, causing displacement of one or more papillary muscles disposed therein. Such papillary muscle displacement may cause or affect leaflet tethering, loss of coaptation, and/or a regurgitant flow path. Although certain embodiments are disclosed herein in the context of left ventricular papillary muscle adjustment or manipulation, it should be understood that the principles disclosed herein are applicable to the right ventricle, and associated anatomy and conditions.

In some implementations, embodiments of the present disclosure provide for treatment for patients suffering from infarction on the inferior wall of the ventricle(s). Such patients may suffer from relatively limited annular dilation, but significant dilation of the inferior wall, causing the posteromedial papillary muscle(s) to distend laterally and/or apically. Distention of the papillary muscle(s) can result in a regurgitant jet or flow at or near the medial scallop (P3) of the posterior leaflet of the mitral valve. Certain embodiments disclosed herein advantageously provide a subvalvular solution for mitral regurgitation through papillary muscle approximation, which may be suitable due to the relatively limited annular dilation that may be experienced by patients suffering from myocardial infarction. The terms "approximation" and "papillary muscle approximation" are used herein according to their broad and/or ordinary meanings, and may refer to the manipulation or adjustment of a papillary muscle to bring the papillary muscle in closer proximity to another papillary muscle or anatomy of the heart.

In some implementations, papillary muscle approximation can be performed surgically. Papillary muscle approximation procedures may provide for at least partial reduction in left (and/or right) ventricular volume, reduction in recurrent mitral regurgitation, and/or other improvement in cardiac function. However, with respect to surgical solutions, such surgeries may be relatively difficult to teach and/or perform. Therefore, it may be desirable to implement papillary muscle approximation through percutaneous approaches, which may provide access to therapy treating the underlying cause of functional mitral regurgitation to increased numbers of patients and/or physicians.

Figure 2:
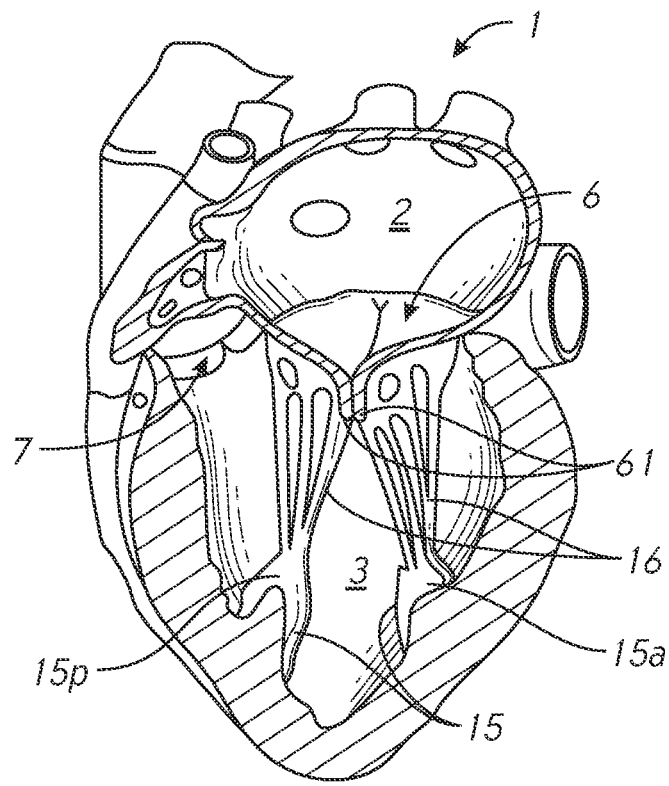
FIG. 2 provides a cross-sectional view of the left ventricle and left atrium of an example heart.

FIG. 2 provides a cross-sectional view of the left ventricle 3 and left atrium 2 of an example heart 1. The diagram of FIG. 2 shows the mitral valve 6, wherein the disposition of the valve 6, papillary muscles 15 and/or chordae tendineae 16 may be illustrative as providing for proper coapting/coaptation of the valve leaflets 61 to advantageously at least partially prevent regurgitation and/or undesirable flow into the left atrium from the left ventricle 3, and vice versa. Although a mitral valve 6 is shown in FIG. 2 and various other figures provided herewith, and described herein in the context of certain embodiments of the present disclosure, it should be understood that papillary muscle adjustment principles disclosed herein may be applicable with respect to any atrioventricular valve and/or associated anatomy (e.g., papillary muscles, chordae tendineae, trabeculae carneae, ventricle wall, etc.), such as the tricuspid valve.

As described above, with respect to a healthy heart valve as shown in FIG. 2, the valve leaflets 61 may extend inward from the valve annulus and come together in the flow orifice to permit flow in the outflow direction (e.g., the downward direction in FIG. 2) and prevent backflow or regurgitation in the inflow direction (e.g., the upward direction in FIG. 2). For example, during atrial systole, blood flows from the atrium 2 to the ventricle 3 down the pressure gradient, resulting in the chordae tendineae 16 being relaxed due to the atrioventricular valve 6 being forced open. When the ventricle 3 contracts during ventricular systole, the increased blood pressures in both chambers may push the valve 6 closed, preventing backflow of blood into the atria 2. Due to the lower blood pressure in the atria compared to the ventricles, the valve leaflets may tend to be drawn toward the atria. The chordae tendineae 16 can serve to tether the leaflets and hold them in a closed position when they become tense during ventricular systole. The papillary muscles 15 provide structures in the ventricles for securing the chordae tendineae and therefore allowing the chordae tendineae to hold the leaflets in a closed position. The papillary muscles 15 may include an anterolateral papillary muscle 15a, which may be tethered to the posterior leaflet, for example, and a posteromedial papillary muscle 15p, which may be tethered to the anterior leaflet, for example. With respect to the state of the heart 1 shown in FIG. 2, the proper coaptation of the valve leaflets, which may be due in part to proper position of the papillary muscles 15, may advantageously result in mitral valve operation substantially free of leakage.

Figure 3:
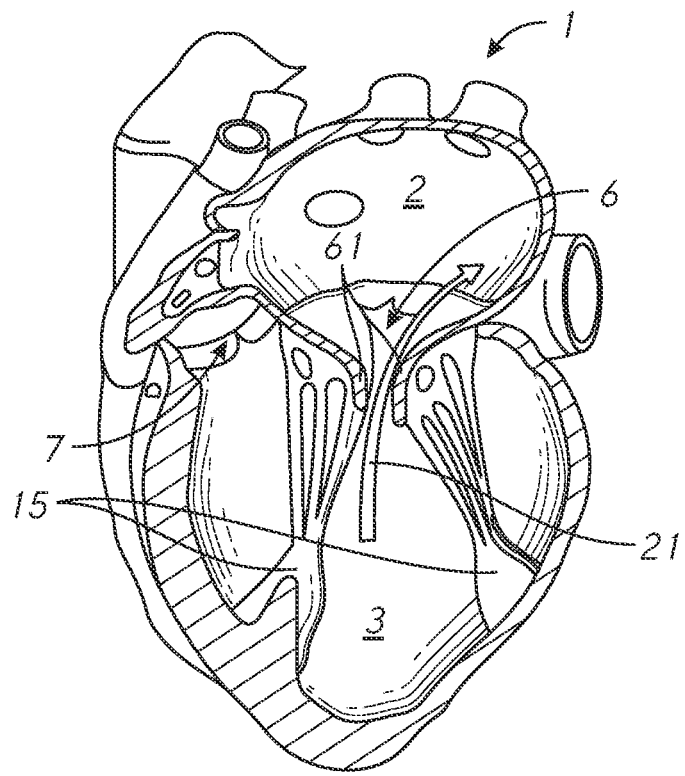
FIG. 3 provides a cross-sectional view of a heart experiencing mitral regurgitation.

Heart valve disease represents a condition in which one or more of the valves of the heart fails to function properly. Diseased heart valves may be categorized as stenotic, wherein the valve does not open sufficiently to allow adequate forward flow of blood through the valve, and/or incompetent, wherein the valve does not close completely, causing excessive backward flow of blood through the valve when the valve is closed. In certain conditions, valve disease can be severely debilitating and even fatal if left untreated. With regard to incompetent heart valves, over time and/or due to various physiological conditions, the position of papillary muscles may become altered, thereby potentially contributing to valve regurgitation. For example, as shown in FIG. 3, which illustrates a cross-sectional view of a heart 1 experiencing mitral regurgitation flow 21, dilation of the left ventricle may cause changes in the position of the papillary muscles 15 that allow flow 21 back from the ventricle 3 to the atrium 2. Dilation of the left ventricle can be caused by any number of conditions, such as focal myocardial infarction, global ischemia of the myocardial tissue, or idiopathic dilated cardiomyopathy, resulting in alterations in the geometric relationship between papillary muscles and other components associated with the valve(s) that can cause valve regurgitation. Functional regurgitation may further be present even where the valve components may be normal pathologically, yet may be unable to function properly due to changes in the surrounding environment. Examples of such changes include geometric alterations of one or more heart chambers and/or decreases in myocardial contractility. In any case, the resultant volume overload that exists as a result of an insufficient valve may increase chamber wall stress, which may eventually result in a dilatory effect that causes papillary muscle alteration resulting in valve dysfunction and degraded cardiac efficiency.

With further reference to FIG. 3, the heart 1 is shown in a state where functional mitral valve regurgitation is present. Functional mitral valve regurgitation may be considered a disease of the left ventricle 3, rather than of the mitral valve 6. For example, mitral valve regurgitation may occur when the left ventricle 3 of the heart 1 is distorted or dilated, displacing the papillary muscles 15 that support the two valve leaflets 61. The valve leaflets 61 therefore may no longer come together sufficiently to close the annulus and prevent blood flow back into the atrium 2. If left untreated, the functional mitral valve regurgitation experienced in the state shown in FIG. 3 may overload the heart 1 and can possibly lead to or accelerate heart failure. Solutions presented herein provide devices and methods for moving the papillary muscles 15 closer to their previous position, which may advantageously reduce the occurrence of mitral regurgitation.

As shown in FIG. 3, the leaflets 61 of the mitral valve (or tricuspid valve) are not in a state of coaptation, resulting in an opening between the mitral valve leaflets 61 during the systolic phase of the cardiac cycle, which allows the leakage flow 21 of fluid back up into the atrium 2. The papillary muscles 15 may be displaced due to dilation of the left ventricle 3, or due to one or more other conditions, as described above, which may contribute to the failure of the valve 6 to close properly. The failure of the valve leaflets 61 to coapt properly may result in unwanted flow in the outflow direction (e.g., the upward direction in FIG. 3) and/or unwanted backflow or regurgitation toward the inflow direction (e.g., the downward direction in FIG. 2).

Certain embodiments disclosed herein provide solutions for incompetent heart valves that involve papillary muscle re-positioning and/or adjustment. Solutions presented herein may be used to at least partially change the position of one or more papillary muscles in order to reduce the occurrences and/or severity of regurgitation, such as mitral regurgitation. Mitral valve regurgitation often may be driven by the functional/physical positioning changes described above, which may cause papillary muscle displacement and/or dilatation of the valve annulus. As the papillary muscles move away from the valve annulus, the chordae tendineae connecting the muscles to the leaflets may become tethered. Such tethering may restrict the leaflets from closing together properly, either symmetrically or asymmetrically, depending on the relative degree of displacement between the papillary muscles. Moreover, as the annulus dilates in response to chamber enlargement and increased wall stress, increases in annular area and changes in annular shape may increase the degree of valve insufficiency.

Various techniques that suffer from certain drawbacks may be implemented for treating mitral valve dysfunction, including surgical repair or replacement of the diseased valve or medical management of the patient, which may be appropriate or effective primarily in early stages of mitral valve dysfunction, during which levels of regurgitation may be relatively low. For example, such medical management may generally focus on volume reductions, such as diuresis or afterload reducers, such as vasodilators, for example. Valve replacement operations may also be used to treat regurgitation from valve dysfunction. However, such operations can result in ventricular dysfunction or failure following surgery. Further limitations to valve replacement solutions may include the potential need for lifelong therapy with powerful anticoagulants in order to mitigate the thromboembolic potential of prosthetic valve implants. Moreover, in the case of biologically-derived devices, such as those used as mitral valve replacements, the long-term durability may be limited. Another commonly employed repair technique involves the use of annuloplasty rings to improve mitral valve function. An annuloplasty ring may be placed in the valve annulus and the tissue of the annulus sewn or otherwise secured to the ring. Annuloplasty rings can provide a reduction in the annular circumference and/or an increase in the leaflet coaptation area. However, annuloplasty rings may flatten the saddle-like shape of the valve and/or hinder the natural contraction of the valve annulus. In addition, various surgical techniques may be used to treat valve dysfunction. However, such techniques may suffer from various limitations, such as requiring opening the heart to gain direct access to the valve and the valve annulus. Therefore, cardiopulmonary bypass may be required, which may introduce additional morbidity and mortality to the surgical procedures. Additionally, for surgical procedures, it can be difficult or impossible to evaluate the efficacy of the repair prior to the conclusion of the operation.

Disclosed herein are devices and methods for treating valve dysfunction without the need for cardiopulmonary bypass and without requiring major remodeling of the dysfunctional valve. In particular, passive techniques to change the shape and/or position of the papillary muscles are disclosed for reducing regurgitation while maintaining substantially normal leaflet anatomy. Furthermore, various embodiments disclosed herein provide for the treatment of valve dysfunction that can be executed on a beating heart, thereby allowing for the ability to assess the efficacy of the papillary muscle re-positioning treatment and potentially implement modification thereto without the need for bypass support.

With respect to percutaneous approaches or solutions for papillary muscle approximation, certain anatomy of the ventricular chamber may present certain challenges with respect to the navigation of papillary muscle approximation and/or engagement/anchoring tools or devices therein. Such anatomy can make the securing of papillary muscles and/or means or mechanisms for approximating or bringing the play muscles together relatively challenging. For example, papillary muscle shape, size, and/or the number of heads or forms associated with papillary muscles may vary from patient-to patient. Devices and methods for ventricular reshaping may therefore advantageously utilize implant and/or anchoring devices designed to navigate the complex inner anatomy of the ventricle.

In some implementations, the present disclosure provides devices and methods for eliminating or reducing mitral regurgitation at least in part by reducing left ventricular volume and/or relieving leaflet tethering via papillary muscle approximation. Such devices/methods may advantageously utilize coil and/or spring-like devices or mechanisms. Although certain surgical procedures may be implemented for papillary muscle approximation, as described above, embodiments of the present disclosure advantageously provide for percutaneous access to the papillary muscles and/or associated anatomy, which may be safer and/or easier to execute relative to certain surgical procedures, and therefore may allow for a relatively greater number or percentage of potential patients to be eligible for valve treatment through papillary muscle approximation.

Coil Implant Devices

Certain embodiments disclosed herein provide for systems, devices and methods for adjusting the position of papillary muscles in the left and/or right ventricles of a heart in order to improve valve coaptation during ventricular systole. For example, in some implementations, the present disclosure relates to percutaneous sub-valvular implants for the left or right ventricle that are designed to at least partially reduced mitral regurgitation by relieving leaflet tethering via papillary muscle approximation using spring and/or coil mechanism(s). The use of coils and/or springs in papillary muscle approximation and/or other tissue anchoring or implantation solutions for the left and right ventricles can provide certain advantages. For example, such devices may be relatively effective at navigating the often-challenging anatomy within the ventricle(s) (e.g., left ventricle). Furthermore, such devices may comprise features or forms that may further be utilized as anchor mechanisms to provide stress relief associated with the tensioning of papillary muscles and/or associated anatomy.

Unlike certain annular solutions, which may target the downstream effects of papillary muscle and/or chordae tendoneae a tethering (e.g. as may result from annular dilation and may lead to recurrent mitral regurgitation, for example), sub-valvular percutaneous solutions in accordance with the present disclosure may directly treat the primary cause(s) of mitral regurgitation in patients with inferior infarcts, including ventricular dilation and resulting papillary muscle dislocation. Therefore, solutions disclosed herein may advantageously be targeted to a subset of functional mitral regurgitation patients in some implementations, such as those with inferior infarcts, rather than or in addition to annular dilation.

Figure 4:
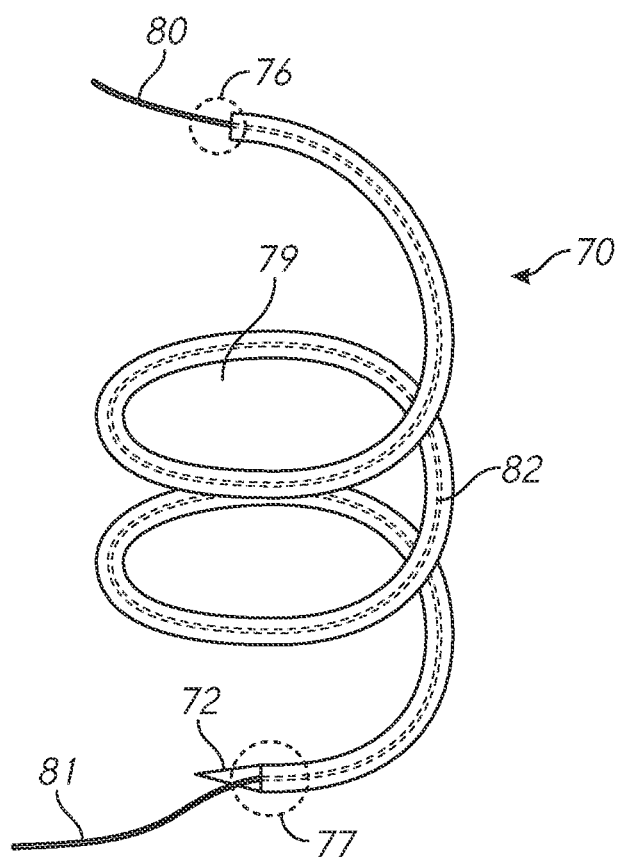
FIG. 4 is a perspective view of a helical coil implant device in accordance with one or more embodiments.

Papillary adjustment devices disclosed herein may be implanted independently in one of the ventricles of the heart. Such devices may be introduced into the patient system through surgical or, advantageously, minimally-invasive means. FIG. 4 is a perspective view of a helical coil implant device in accordance with one or more embodiments. In some embodiments, the helical coil device 70 is configured to encircle and/or pierce at least a portion of a papillary muscle for anchoring thereto and/or applying tension thereto. Papillary muscle approximation and/or other types of coil-based tissue anchoring and/or approximation may be achieved using a delivery catheter through, for example, a transseptal operation. The helical coil implant 70 may be deployed starting at a tip portion of a papillary muscle in some implementations. In certain embodiments, the coil implant 70 comprises a needle-, or pointed tip 72 at or near a distal end 77 of the coil 70. The needle tip 72 and/or distal end 77 of the coil 70 may be attached to a suture 80/81, which may be disposed at least partially within the coil 70 and/or otherwise secured thereto throughout at least a portion of the coil, as shown. In connection with implantation of the coil 70, as the coil exits a delivery catheter used to deliver the coil 70 to the target anatomy/location, the pointed tip 72 may be used to pierce the tip or other portion of a target papillary muscle. The coil 70 may then be, for example, rotated to drive the distal end 77 of the coil towards the base of the papillary muscle and/or other associated tissue. In some implementations, the motion of winding the coil 70 during implantation may allow for at least partial (e.g., complete) encircling of papillary muscles of varying geometries.

In one example implementation, a separate coil implant may be deployed at or about one or more papillary muscles of a target ventricle, such as the left ventricle. For example, coil implants in accordance with the embodiment of FIG. 4 may be implanted at the anterior and posterior papillary muscles, respectively, of the left ventricle. Once deployed, sutures associated with each of the coil implants may be fed and/or drawn between or from the end(s) of the respective coils and joined in some manner, such as to provide tension and/or a tethering effect between the two (or three) coil implants, and therefore between the papillary muscles associated therewith. The feeding and/or manipulation of sutures from within the coil(s) may be performed using a separate delivery catheter than the delivery catheter used to deliver the coil 70 to the target location in the ventricle.

Figure 5:
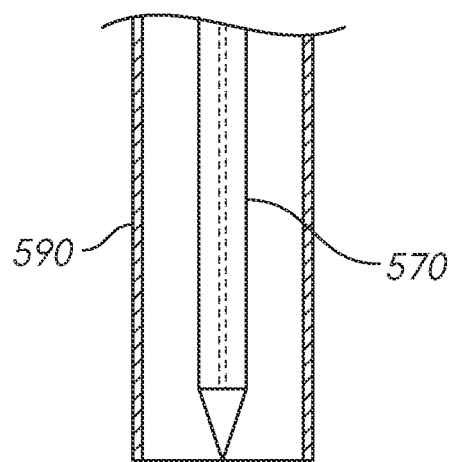
FIG. 5 a cross-sectional view of an implant device in a crimped configuration in a catheter in accordance with one or more embodiments.

The diagram of FIG. 4 shows the coil 70 comprising a needle tip 72 and an inner suture 82 disposed at least partially within, or otherwise secured to, the coil form 70. FIG. 5 illustrates a cross-sectional view of a coil implant device 570 (e.g., such as the coil 70 shown in FIG. 4) in an at least partially crimped state or position within a delivery catheter 590. The coil 570 may comprise, for example, shape memory metal or other material, wherein the coil may be pulled or pushed into the catheter 590 to force the coil into a relatively small profile configuration. For example, the catheter 590 may be a relatively small profile catheter, which may advantageously facilitate delivery thereof through percutaneous means. Although FIG. 5 shows the coil 570 in a crimped state, in some embodiments, tissue engagement coil implants in accordance with the present disclosure are transported in a delivery catheter in a coiled state. For example, at least partially rigid coil implants may be carried in a relatively large-bore catheter, wherein the coil implant is not substantially crimped or straightened-out in the catheter.

The shape and/or form of the coil implant device 70 may help in navigating the anatomy of the ventricle, such as that of the chordae tendineae, trabeculae carneae, and/or papillary muscles. The coil implant device 70 may be used to anchor to and/or engage a papillary muscle in a way that is not substantially obstructed or interfered with by the local anatomy. Furthermore, the coiled shape of the implant device 70 may provide for a relatively large amount of surface contact area between the anchor device 70 and the proximal tissue. In some embodiments, the coil implant device 70 includes surface treatment feature(s), such as one or more microanchors/barbs, abrasive surface elements or treatments, or the like, which may help to at least partially prevent the backing-out or unwinding of the coil 70 after implantation thereof. Such anchoring features may be designed such as to advantageously not undesirably damage tissue with which they are in contact. The relatively large amount of surface area for tissue engagement of the coil device 70 may serve to increase retention force for the device 70 when deployed.

As the coil implant 70 is wound into and/or about a papillary muscle or other anatomical feature of the ventricle of a heart, tissue may be passed at least partially out an upper end or opening 79 of the coil. Although certain embodiments are disclosed herein in the context of using coil implants to engage papillary muscle tissue, it should be understood that coil devices/anchors in accordance with the present disclosure may be used to engage any type of tissue or material. When engaged in tissue, the coil device 70 may provide an anchoring point, which may allow for manipulation and/or tensioning of tissue with which the coil device 70 is engaged.

The suture 82 associated with the coil implant device 70 may run along at least a portion or length of the coil 70, and may exit or be drawn from the coil at one or both ends thereof. For example, a first end 80 of the suture may extend from a proximal end portion 76 of the coil implant 70, while a second end 81 of the suture may extend from the distal end portion 77. Although the suture 82 is illustrated in FIG. 4 as exiting both distal and proximal ends of the coil implant 70, in some implementations, the suture may exit only the proximal end 76. Furthermore, in some implementations, the suture may be attached to the coil implant 70, but may not run along the coils thereof within the coils as shown in FIG. 4. However, where the suture is drawn from, or connected to, only one end of the coil device 70, force applied thereto may cause undesirable unwinding of the coil device 70 out of the engaged anchoring position/tissue. Alternatively, as shown in FIG. 4, the ends 80, 81 of the suture may be used to provide two anchoring forces or vectors, which may advantageously distribute the load on the implant 70 over the length thereof to a greater degree than in single-ended suture attachment embodiments. In order to allow for the end 81 of the suture to be drawn out the distal end 77 of the coil implant 70, the coil may advantageously provide an aperture or other feature through which the end 81 of the suture may be fed or drawn. In some implementations, the implant 70 may be implanted with the end 81 of the suture already extending from the distal end 77 of the device.

In some implementations, the coil implant 70 may be preloaded with, for example, a small gauge wire or the like. Such wire may be fed through the coil, such as out the distal end 77 thereof, wherein the wire may be grabbed or snared in order to pull the wire through the coil and allow a suture attached to a proximal end or portion of the coil to be drawn through the coil as the guide wire is pulled out of the coil. Although coil devices, such as that shown in FIG. 4, are described herein in certain contexts as being used for papillary muscle approximation and anchoring, it should be understood that coil implant devices in accordance with the present disclosure may be used for any type of tissue anchoring and/or ventricular remodeling application.

Figure 6:
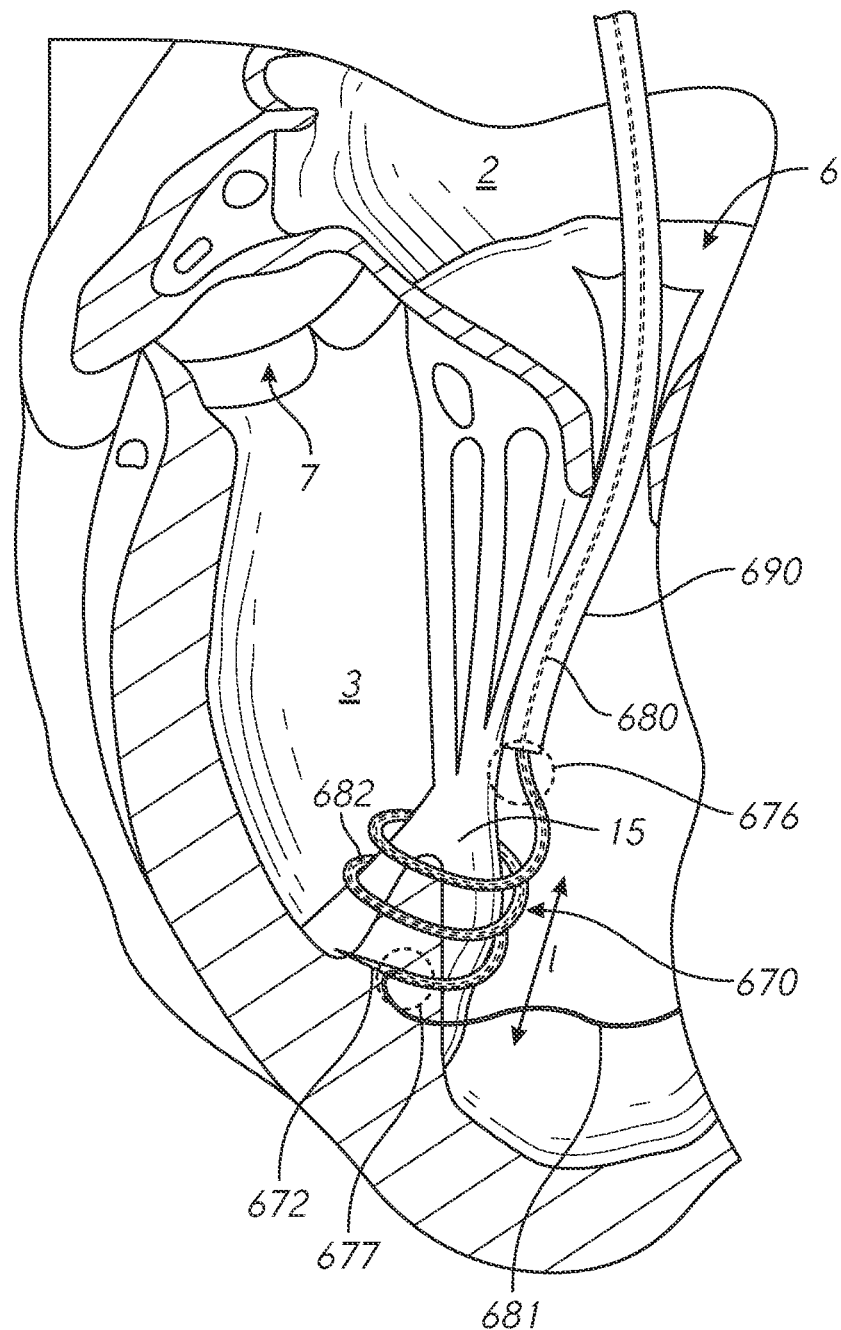
FIG. 6 illustrates a delivery system for a papillary muscle engagement system in accordance with one or more embodiments.

FIG. 6 illustrates a cross-sectional view of a ventricle 3 of a heart, such as a left ventricle, having deployed or provided therein a coil anchor device 670 in accordance with embodiments of the present disclosure. Although certain disclosure herein is presented in the context of the left ventricle and associated anatomy (e.g., valves, papillary muscles, chordae tendineae, ventricle wall, etc.), it should be understood that the principles disclosed herein may be applicable in any ventricle of the heart (e.g., right ventricle) and associated anatomy (e.g., tricuspid valve, papillary muscles, chordae tendineae, ventricle wall, etc.). As described above, in a normal heart, the papillary muscles may contract during the heart cycle to assist in maintaining proper valve function. Reductions in, or failure of, the papillary muscle function can contribute to valve dysfunction and/or regurgitation, which may be caused by infarction at or near the papillary muscle, ischemia, or other causes, such as idiopathic dilated cardiomyopathy, for example.

The diagram of FIG. 6 illustrates the coil implant 670 as wound about a papillary muscle 15, as described above. The coil implant 670 may be delivered to the target implant location using a delivery catheter 690, which is shown as being approximated to the papillary muscle 15. The coil implant 670 may pierce the papillary muscle 15 and/or tissue proximal thereto at any desirable location. Although the coil 670 is illustrated as winding around the papillary muscle 15, it should be understood that coil anchor devices in accordance with the present disclosure may be used to puncture a papillary muscle, such that winding of the coil winds the coil through the tissue of the papillary muscle or one or more portions thereof. In some implementations, the coil 670 may pierce the papillary muscle 15 at or about a tip, base, and/or anywhere along the length 1 thereof. Winding of the coil 670 may wind the coil or portions thereof at least partially within the papillary muscle 15. For example, in some implementations, when deployed in or about the papillary muscle 15, at least a portion of the coil 670 may be disposed within the papillary muscle, while another portion of the coil may be external thereto. In some implementations, synthetic or artificial chordae devices or features may be attached between the coil implant 670 and one or more leaflets of a valve 6 (e.g., mitral valve) associated with the papillary muscle 15. Such artificial chordae may comprise, for example, polytetrafluoroethylene (PTFE), or any other material.

Once fully deployed within the ventricle, the coil implant 670 may provide a substantially permanent implant for the ventricle 3, which may advantageously provide continual papillary muscle tensioning/approximation functionality for the ventricle. In some implementations, the coil device 670 may be used to implant or deploy a rivet, bulky knot, or other type of tissue anchor in the papillary muscle tissue, or other tissue of the ventricle, wherein the coil 670 may be removed from the ventricle in connection with a percutaneous operation, allowing the deployed anchor to remain and provide papillary muscle approximation and/or other functionality in the ventricle after removal of the coil. In some embodiments, the coil implant 670 has a distal end 677 that may be at least partially embedded in tissue of the ventricle (e.g., at or near the apex of the ventricle/heart) and/or papillary muscle. For example, the distal end 677 may have a pointed tissue engagement tip 672, which may facilitate piercing of ventricular tissue. Embedding at least a portion of the distal end portion 677 of the coil implant 670 may help secure the coil implant in an implanted position.

In some implementations, as described above with reference to FIG. 4, the coil implant 670 may have suture portions associated therewith, wherein a suture portion is associated with each of a proximal end 676 and a distal end 677 of the coil 670. For example, the diagram of FIG. 6 illustrates a portion 681 of the suture 680 that is drawn from the distal end 677 of the coil 670. Such suture portion 681 may be coupled to a suture associated with a second coil device (not shown), wherein such coupling may be used to provide tensioning between the two implanted coils. The second coil may be, for example, implanted on or about a second papillary muscle (not shown) of the ventricle. Tensioning of the suture(s) connecting the first coil and the second coil may provide approximation force for drawing papillary muscles associated with the respective coils together. Further, a portion of the suture 680 may exit the coil 670 at or near the proximal portion 676, wherein such proximal suture portion 680 may be coupled to a suture portion of the other implanted coil device (not shown) within the ventricle 3. The coupling of suture portions between the two implanted coil devices may advantageously provide tension vectors between the papillary muscles or other tissue associated with the implanted coil devices that are at least partially normal or orthogonal to the length l of the coil/papillary muscle. Therefore, by using two suture ends to provide tension points for the coil 670, the approximation force between two implanted coils may be distributed at least partially over a length or portion of the coil implant(s). The respective suture portions of the coupled implanted coils may be physically tied or coupled in any suitable or desirable way. For example, such suture portions may be clamped, tied, adhered, or otherwise coupled in order to allow for tensioning thereof. The suture 682 may be generally free to slide within the coil 670, or may be fixed to the coil at one or more points. In some implementations, the adjustment of the proximal suture portion(s) 680 may be used to prevent or treat leaky valve conditions, whereas adjustment/tightening of the base suture portion(s) 681 may be used for ventricular dilation treatment, or other treatments.

Figure 7:
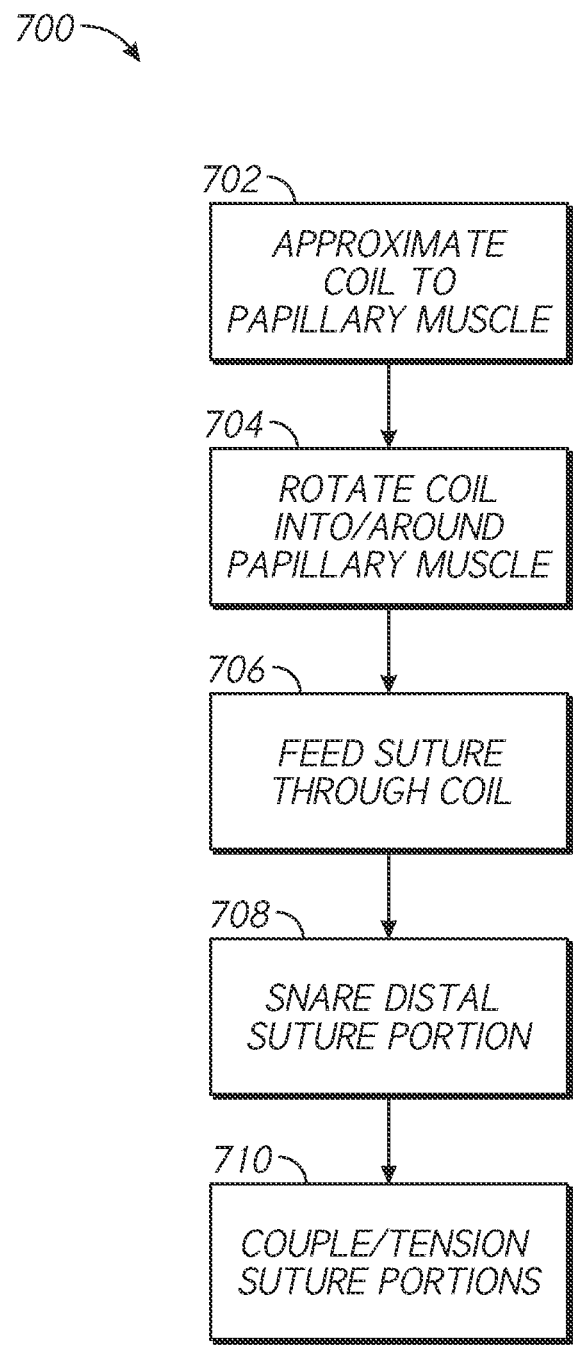
FIG. 7 is a flow diagram for a process for engaging and/or manipulating a papillary muscle in accordance with one or more embodiments.

FIG. 7 is a flow diagram illustrating a process for approximating papillary muscles in accordance with one or more embodiments. The process 700 may be implemented using one or more helical coil implants, which may comprise one or more of a needle tip for puncturing papillary tissue or other tissue, a suture and/or wire that runs through at least a portion of the length of the coil, and an outer sleeve configured to contain and/or secure the suture therein. The helical coil implant device may be configured to be at least partially compressed within a delivery catheter in some embodiments.

At block 702 the process 700 involves approximating a coil anchor to a papillary muscle. At block 704, the process 700 involves rotating or spiraling the coil/anchor into, or at least partially around, the papillary muscle to engage the coil therewith and thereby implant the coil in and/or about the papillary muscle.

At block 706, the process 700 involves feeding a suture through the implanted coil to allow the suture to be expelled and/or drawn from a distal end portion of the coil implant. At block 708, the process 700 involves snaring the suture portion projecting from the distal end of the coil implant. At block 710, the process 700 involves tying or otherwise coupling the distal suture portion with a suture portion associated with a second implant, to thereby allow for tensioning between the two implants. The process may involve pulling the suture portions to a desired tension in order to produce a desired result with respect to valve leaflet coaptation, mitral regurgitation, and/or other cardiac condition. The suture portions may be tied-off or locked in any suitable or desirable way, such as using nanoclips, or the like.

Torsion Spring Devices

Figure 8:
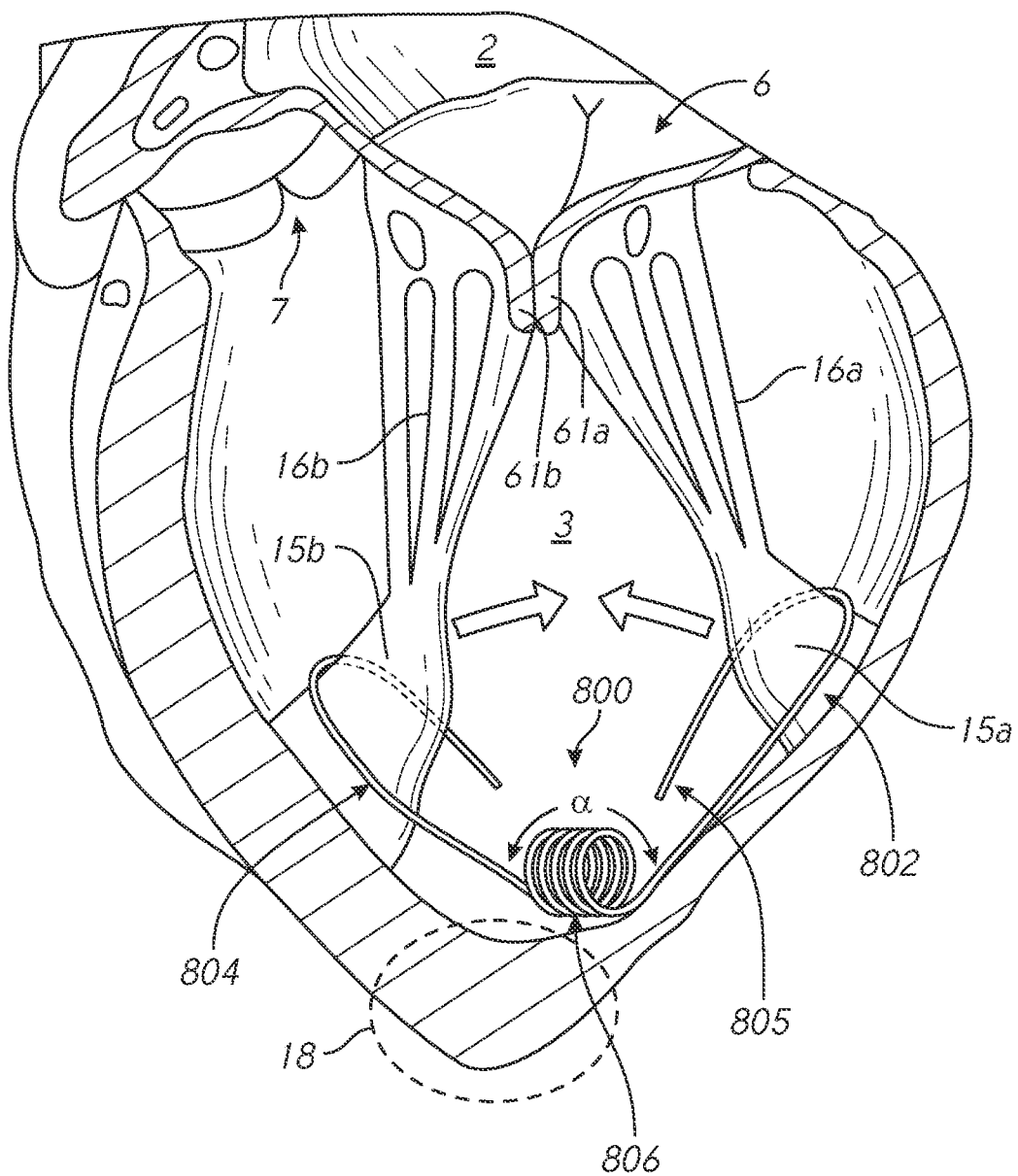
FIG. 8 illustrates a torsion spring device deployed in a ventricle of a heart in accordance with one or more embodiments.

In some implementations, papillary muscle approximation may be achieved using a torsion spring device, or other spring-type device, deployed within the ventricle of the heart. FIG. 8 illustrates a torsion spring device 800 deployed in a heart in accordance with one or more embodiments. In some implementations, a torsion spring device may be delivered to the left ventricle of the heart using a transcatheter operation (e.g., transseptal, transaortic, transapical, etc.). For example, a torsion spring device 800 as shown in FIG. 8 may be deployed at or near the apex region 18 of the heart or ventricle. In certain embodiments, the torsion spring device 800 includes one or more arm members, such as a first arm member 802 and a second arm member 804. In some implementations, each of the arms of the implant device 800 is configured and/or designed to be wrapped or otherwise disposed around or in a separate papillary muscle, wherein a central spring or coil element 806 may be configured to subject inward or outward force on the arms. For example, the coil feature 806 may be configured to pull the arms 802, 804 inward to thereby draw the associated papillary muscles inward to provide valve correction in accordance with the present disclosure. That is, a torsion spring device in accordance with the present disclosure may be configured to draw the papillary muscles towards a center of the ventricle using a tension/coil component and one or more arms.

The heads of the papillary muscles may serve as anchoring points for pushing or pulling, depending on the relevant treatment being implemented. For example, for conditions in which the opening-up of the ventricle is desired for treatment, the arms 802, 804 may be configured and/or position to push against the ventricular walls and/or papillary muscles in a direction outward from the center of ventricle. Such treatments may be desired in connection with heart failure with preserved ejection fraction, wherein the heart may suffer from an undesirably small ventricular space, which may be associated with improper or inadequate filling of the ventricle with blood during diastole. Therefore, the arms 802, 804 may advantageously be used to expand the ventricle in order to improve cardiac output and treat restrictive cardiomyopathy.

Rather than pushing outward against the ventricular wall, in some implementations, the torsion spring device 800 may be configured to pull the ventricular walls and/or papillary muscles inward, as described above. One or more of the arm members 802, 804 may be wrapped around the respective papillary muscle or other anatomy of the ventricle and may pull such anatomy inward to thereby decrease the ventricular space and/or adjust the tethering of the valve leaflets 61a, 61b by the chordae tendon 16a, 16b. By wrapping around and/or otherwise anchoring or securing to the papillary muscles, the torsion spring device 800 may provide the ability to pull inward on the ventricular anatomy, which may provide treatment benefits that are not achievable with other devices and mechanisms designed to push outwardly against the ventricular walls.

The central torsion spring element 806 may comprise a torsional spring element, or other mechanism having a preferred state, wherein when the central component 806 is flexed or drawn into a compressed or expanded state, the spring element may at least partially resist such compression/expansion to create a torsion force on the arms 802, 804. For example, for papillary muscle applications, the central spring 806 may resist the outward flexing of the arms 802 804 and exert an inward pulling force to counteract the outward flexing of the papillary muscles, and thereby draw the papillary muscles 15a, 15b generally toward one another to improve valvular leaflet coaptation. Therefore, the central spring component 806 may serve as an active mechanism for manipulating and/or exerting force on papillary muscles and/or other anatomy of the heart.

The arm members 802, 804 may be configured and/or designed to be at least partially wrapped around the papillary muscles, or otherwise engage or be secured to the papillary muscles. For example, either or both of the arm members 802, 804 may be configured to puncture and embed in, or pass through, papillary muscle tissue. For example, an arm member of the torsion spring device 800 may comprise an anchor configured to be embedded within the tissue of the papillary muscle or other tissue of the ventricle. Such anchoring and/or wrapping of the arm members around papillary muscles may be implemented using a catheter that is designed and/or configured to travel or snake around the papillary muscle for the purpose of anchor/arm placement. In some implementations, a papillary muscle engagement arm of the torsion spring device 800 may have a free end 805 configured to be bent around, or otherwise manipulated to wrap around, the papillary muscle. In some embodiments, the arm members 802, 804 comprise shape memory material (e.g. shape memory metal) configured to be deployed in a first shape or configuration, and, in response to some form of stimulus (e.g., temperature and/or electrical stimulus), assume a shape or position around papillary muscle or other anatomy once positioned within the ventricle.

In some embodiments, the central coil component 806 comprises a different material or materials that the arm members 802, 804. For example, in one embodiment, the central coil component 806 comprises stainless steel, memory metal, or other metal, whereas the arm members may comprise plastic, polymer, or the like. In certain embodiments, the coil portion 806 of the device 800 is delivered to the ventricle in its coiled state. Alternatively, the coil portion 806 may be transferred to the ventricle in an elongated or crimped state, wherein the coil may take its coiled shape once deployed within the ventricle. Such coiling in the ventricle may be implemented using a shape memory material. Generally, the environmental temperature associated with the ventricle may be sufficient to effect the shape activation and/or maintain the shape memory coil in a sufficiently rigid desired coil form. In some implementations, shape-memory-based spring devices or components may be delivered to the ventricle using a cooling catheter device configured to maintain such components at a desired temperature that is less than the environmental temperature of the interior of the ventricle. For example, the cooling catheter may be configured to circulate cooling fluid or otherwise maintain a cool temperature therein.

As illustrated in FIG. 8, the torsion spring device 800 may be formed of a single continuous/unitary wire forming the arm members and central spring component 806. Alternatively, the arms may be separate components, at least initially, from the central spring component 806. For example, in some implementations, the arm(s) may be anchored, embedded, or otherwise secured to or wrapped around the papillary muscle(s), wherein the arm(s) may be subsequently attached to the torsion spring element 806 to form a torsion coil papillary muscle approximation assembly.

At least a portion of the arm members 802, 804 may be associated with padding or material designed or configured to prevent tissue damage or erosion from contact with the arm members. For example, an arm member of the torsion spring device 800 may comprise an outer sleeve or portion, which may comprise cloth, polymer, or other material that is not substantially abrasive with respect to the tissue coming in contact therewith. In some embodiments, at least partially rigid wire or other inner member may be disposed within the outer sleeve or in contact therewith to provide the desired rigidity and/or force against the associated tissue. The outer contact sleeve portion of the arm member may also serve to distribute the load force of the arm over a broader surface area.

The torsion spring device 800 may have any suitable or desirable form or shape, such as a leaf spring shape or form. Furthermore, although illustrated as having a generally V-shaped form, the spring device 800 may take a U-shaped form, or other shape or form. The torsion spring device 800 may be set at an angle α that is less than the angle of the arms as anchored, such that, once anchored, the arms exert force to bring the angle between the arms back to, or closer to, the angle α, thereby adjusting papillary muscles and/or leaflets associated therewith.

Helical Cinching Coil Devices

Figure 9:
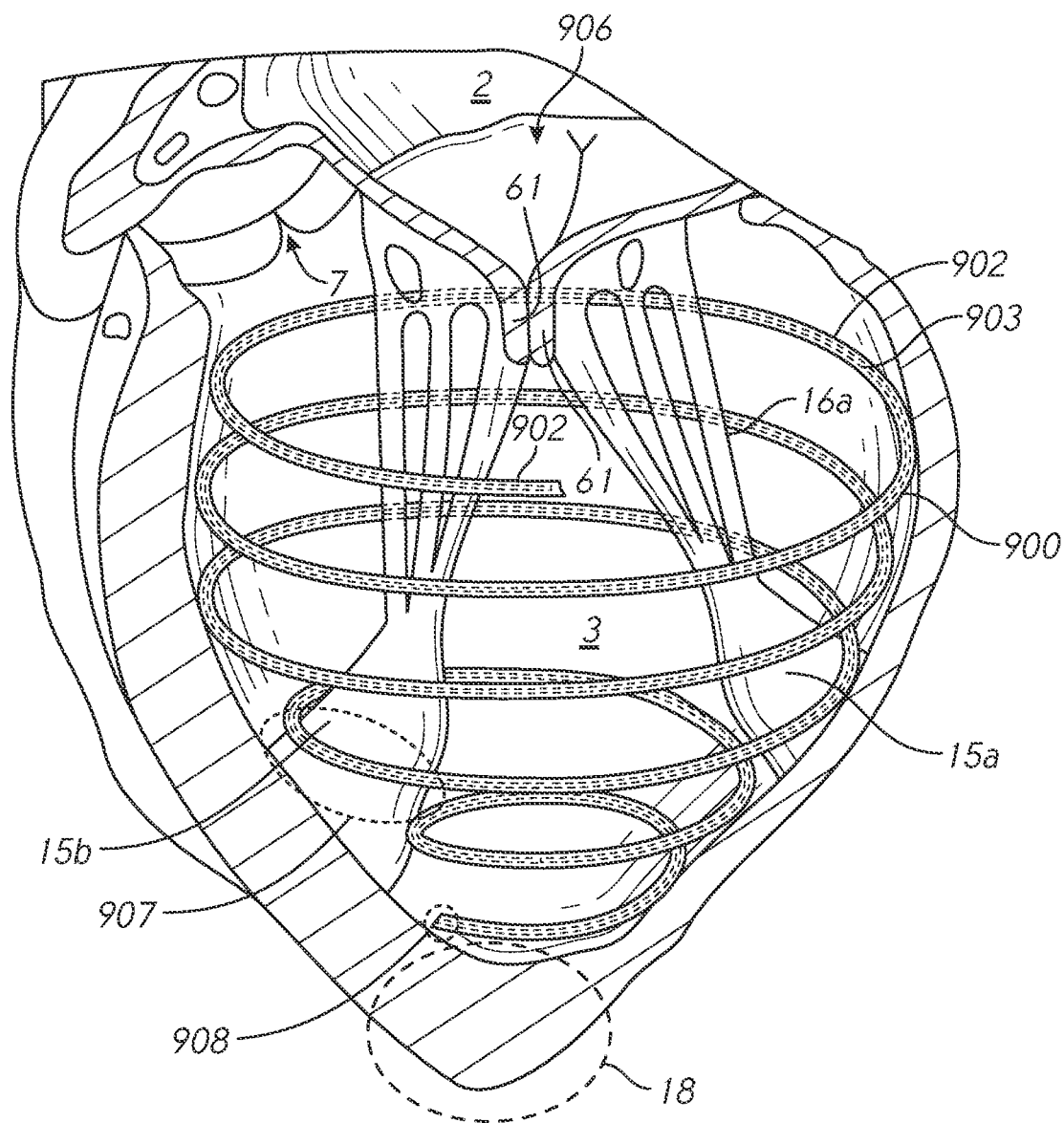
FIG. 9 illustrates a helical ventricle adjustment device deployed in a ventricle of a heart in accordance with one or more embodiments.

FIG. 9 illustrates a papillary muscle and/or ventricle adjustment device 900 in accordance with one or more embodiments. In some implementations, the present disclosure provides a helical cinching device 900, which may generally have a spring-type form or shape. The device 900 may be configured to be delivered to the ventricle of a heart using a transcatheter approach. In certain embodiments, the helical cinching device 900 comprises a relatively large dual-layer helical form that is configured and/or designed to wrap around one or more papillary muscles in the ventricle. For example, the device 900 may comprise an outer layer, which may serve as a passive anchor and/or tissue interface component of the device 900. The device 900 may further comprise an inner layer or component 903 that provides a relatively undersized, strong, passive spring-type element. Such inner component 903 may provide inward or outward cinching or expanding force to thereby manipulate one or more anatomical features of the ventricle 3, such as the papillary muscles 15a, 15b. In some implementations, the outer component 903 may comprise a sleeve, tube, or other form configured to anchor in some manner to the ventricular wall. For example, the outer sleeve component 902 may be associated with one or more microanchors, barbs, or the like, wherein such features may be configured to engage the wall of the ventricle or other anatomy associated therewith in order to provide increased surface contact area for the device 900. In some embodiments, the outer component 902 comprises a full sleeve providing circumferential covering of the inner component 903.

In some embodiments, the inner component 903 comprises a coil or wire form, which may incorporate a spring-type mechanism configured to draw the device 900, and with it the ventricle, inward, or to provide outward force away from the center of the ventricle. The inner component 903 may comprise shape memory metal, or other type of metal or at least partially rigid material. The inner component 903 may advantageously be configured to assume a desired shape memory, such that placement or disposition of the inner component within the outer component 902 causes the outer component 902 to be manipulated to the shape of the inner component.

With the outer component 902 in full or partial contact with the ventricular wall, the inner portion 903, which is secured to and/or contained within the outer portion 902, may exert an inward force along some or all of the ventricle. In addition, at least a portion 907 of the helical coil device 900 may abut one or more of the papillary muscles on an outer side thereof when the coil device 900 is fully deployed and/or introduced to the area of the ventricle containing the papillary muscle(s). When contacting an outer surface or portion of a papillary muscle, the coil device 900 may exert an inward force thereon to thereby move for approximate the papillary muscle(s). Such papillary muscle approximation may advantageously result in valve correction, wherein leaflets 61 of a valve 906 associated with the ventricle 3 (e.g. mitral valve) may be brought into coaptation as to prevent or reduce the occurrence of regurgitation.

In certain embodiments, the outer portion 902 of the coil device 900 comprises cloth or other material or substance configured to promote ingrowth with the tissue in contact therewith. When contacting the tissue of the ventricle, such as the inner wall of the ventricle, the outer portion 902 of the coil device 900 may become fixed to the ventricular tissue over an ingrowth period (e.g., approximately 10 weeks or more). In some implementations, the outer portion 902 of the coil device 900 may be implanted in connection with a first procedure or operation, wherein after tissue attachment between the outer portion 902 and the contacting ventricular tissue has occurred through ingrowth, a secondary procedure may be performed in which the inner portion or component 903 is threaded into or otherwise secured to the outer portion 902.

In certain embodiments, one or more components of the coil device 900 may be integrated with one or more biodegradable elements or spacers, which may be configured and designed to hold one or more of the inner and outer components of the coil device 900 in an expanded or restricted state until a point in time at which such elements/spacers may dissolve or be removed, thereby causing contraction and/or reshaping of the associated components of the device 900. For example, the device 900 may comprise spacers (not shown) that dissolve a period of time after an operation, causing the device and/or components thereof to assume a relatively smaller or contracted shape or form. In some embodiments, the coil device 900 may be implanted with dissolvable sutures or other anchors or attachment mechanisms that are configured to constrain at least a portion of the device 900 in an expanded or restricted state, wherein the device may become free of such expansion/restriction once the sutures/anchors are dissolved or removed, causing the spring effect of the device 900 to assume a desired shape for reshaping or adjusting the ventricular anatomy.

In some embodiments, a distal end portion 908 of the helical coil device 900 is anchored or secured in some manner to the wall or tissue of the ventricle 3. For example, the distal end portion 908 may be anchored to the ventricular tissue at or near the apex portion 18 of the heart/ventricle. Once anchored, tension may subsequently be applied to cinch or draw inward the coils of the helical coil device 900, to thereby reshape the ventricle. In some implementations, the coil implant device 900 may be implanted in association with air pocket, or balloon, devices, which may be configured to be inflated to increase tension, either inward or outward, on the coils of the device 900. Such balloon devices may subsequently be deflated to thereby reshape the device 900 and/or ventricular anatomy. In some implementations, the coil device 900, or portion thereof, may be electrically activatable, wherein an application of an electrical charge may cause the coil device 900, or portion thereof, to expand or contract.

In some embodiments, the coil device 900 may be expanded using one or more biodegradable sutures or spacers, wherein after a period of time such biodegradable features may degrade, such that the coil device may expand or contract in response thereto. For example, the coil device 900 may be expanded and secured to the ventricular wall by biodegradable sutures, wherein when the sutures degraded, the tension in the coil 900 may cause the coil device 902 contract and pull inward from the ventricular wall, thereby reshaping or repositioning the ventricular walls and/or papillary muscles.

In implanting the coil device 900, the trabeculae carneae (not shown) or other anatomy may be targeted for anchoring. For example, the coil may be wrapped at least partially inside or behind trabeculae carneae or other anatomy. In implementations in which the coil 900 is anchored at or near the apex 18 of the heart, as the heart beats, the inner wire component 903 of the coil device 900 may be permitted to slide or move within the outer sleeve 902, which may provide force for moving the ventricle in or out without substantially resisting the actual active beating of the ventricle. In some embodiments, the coil 900 is fixed only at one end 908. As the heart beats, and the ventricle contracts, the inner wire 903 may wind and unwind as the heart contracts and relaxes. The outer sleeve 902 may comprise any suitable or desirable material, such as plastic, metal, or other material. Where the inner wire 903 is configured to move or slide within the outer sleeve 902, it may be desirable for the outer sleeve to comprise material that is strong enough to resist such frictional movement between the inner and outer components, such that the inner wire 903 does not wear through the outer sleeve over time. With respect to anchor devices designed for ingrowth of the outer sleeve 902 with the ventricular tissue, the outer sleeve may advantageously comprise cloth or other material that promotes ingrowth. Alternatively, where the coil device 900 is designed to be anchored to the ventricular wall solely through anchoring with barbs or the like, the outer sleeve 902 or coil device 900 may comprise metal or other material. Although some embodiments are described herein in the context of an inner wire that is able to move or slide relative to the outer sleeve 902, in certain embodiments, the inner component 903 may be fixed to the outer sleeve 902 at one or more points or regions. In the illustrated deployed configuration of FIG. 9, the helical coil device 900 is configured for surrounding both papillary muscles 15*a*, 15*b*, wherein the coil device 900 is a dual-layer device, comprising a passive outer tissue interface layer, as well as an inner spring-type layer configured and designed to promote cinching or expansion of the coil device 900.

Apex Cinching Clip Devices

Figure 10:
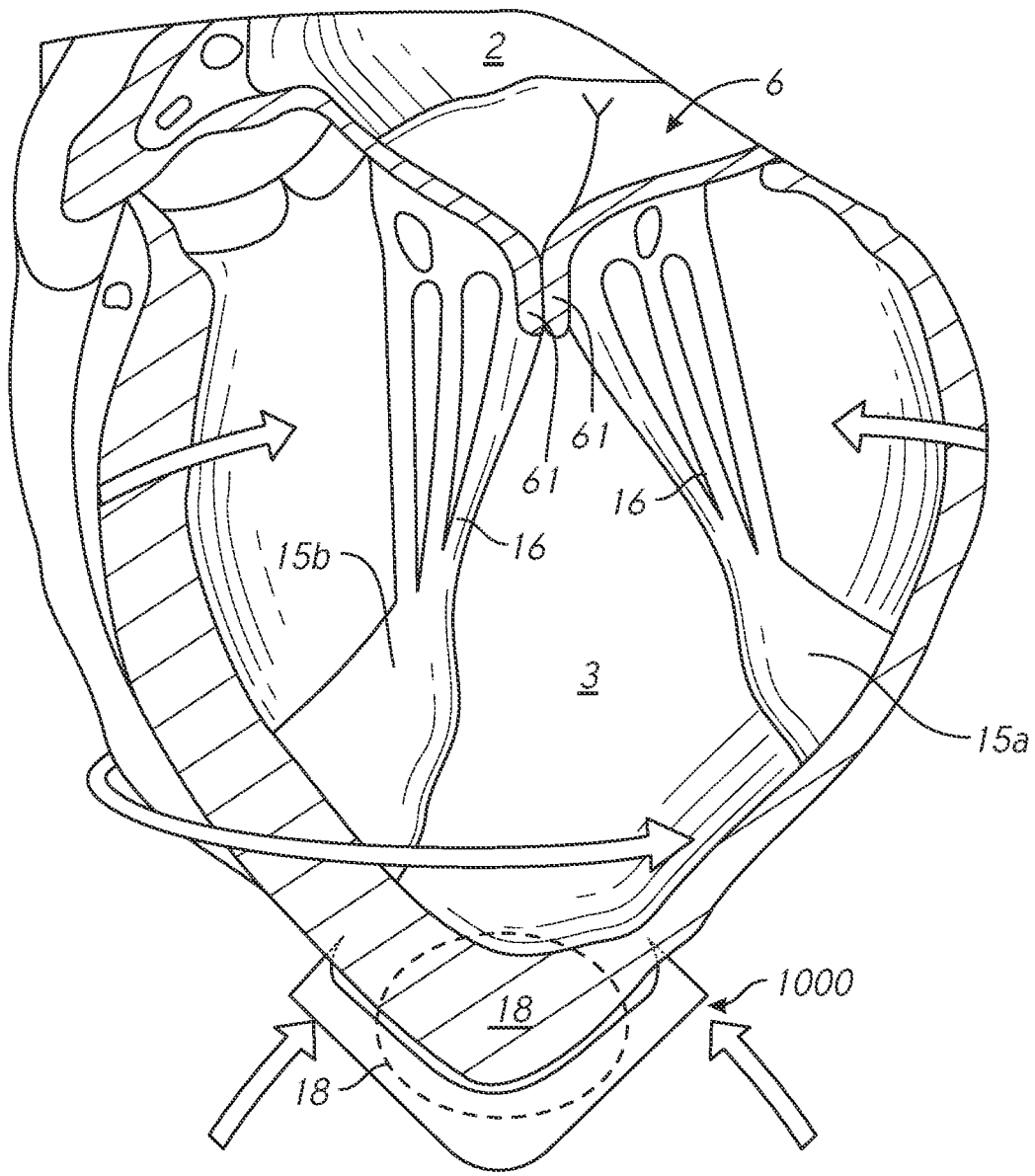
FIG. 10 illustrates a pericardial leveraging clip device engaged with a pericardium of a heart in accordance with one or more embodiments.

FIG. 10 illustrates a ventricle adjustment device 1000 configured to utilize pericardial leveraging to cinch the ventricle to a restricted or tightened shape or position. The ventricle adjustment device 1000 may be considered a ventricular apex cinching clasp, clip, or spring, which may be deployed at or near the apex 18 of the left ventricle 3, for example. Although illustrated as a clip device, in some embodiments, the ventricular restraint device 1000 comprises a spring form or device configured to be twisted into or about the apex to thereby restrict ventricular dilation and achieve papillary muscle approximation. In some implementations, the ventricular restraint device 1000 comprises a coil or the like.

In some implementations, the ventricular restraint device 1000 may be deployed by twisting and/or cinching the pericardium, or pericardial sac, of the heart/ventricle. In some embodiments, the pericardium and/or pericardial sac is squeezed rather than, or in addition to, being twisted/cinched, to at least partially remodel and/or restrain the ventricle, as described and shown. Once twisted, cinched, or squeezed to restrain the ventricle, the ventricular restraint device 1000 may be clipped on the pericardium at or around the apex 18 to maintain the restraint of the ventricle achieved through twisting or cinching. In some implementations, the restraint device 1000 is engaged primarily with the pericardial sac portion of the exterior of the heart.

When the ventricular restraint device 1000 is engaged with the pericardial sac, any increase in pericardial pressure caused by the cinching of the pericardium may advantageously equalize over time, such that tamponade or other adverse conditions may not ultimately be caused by implantation of the device 1000. For example, cardiac tamponade may involve the fluid in the pericardial sac around the heart becoming pressurized such that a pressure differential between the pericardial sac and the chamber(s) of the heart reduces the ability of the heart to relax and accept blood during diastole. Generally, the ventricular restraint device 1000 may be clamped on the pericardium of the heart in such a way as to restrain the ventricle without overly pressurizing the pericardial sac relative to the adjacent chambers.

Papillary Muscle Approximation Hoop/Spiral Devices

Figure 11:
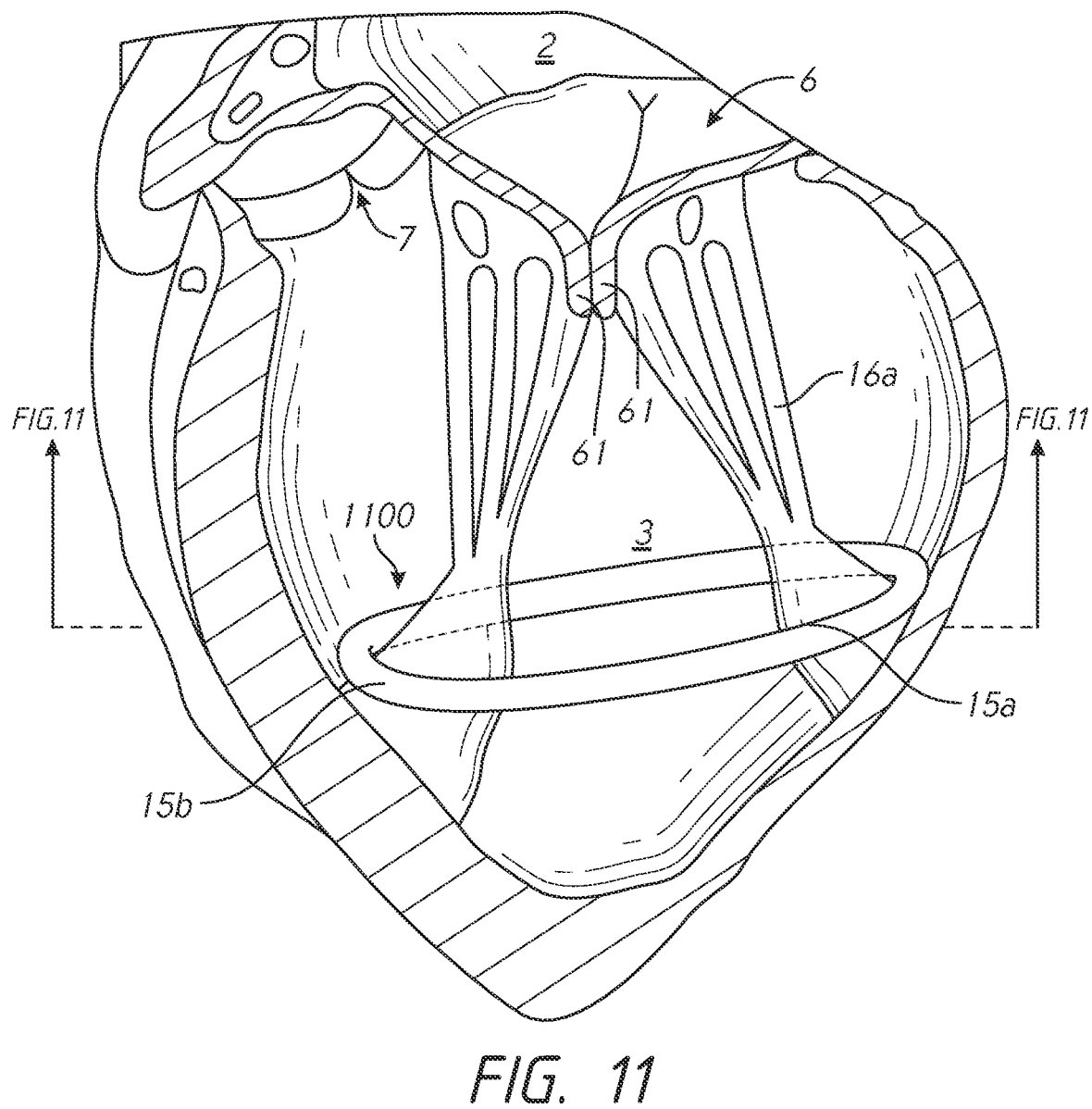
FIG. 11 illustrates a papillary muscle adjustment device deployed in a ventricle of a heart in accordance with one or more embodiments.
Figure 12:
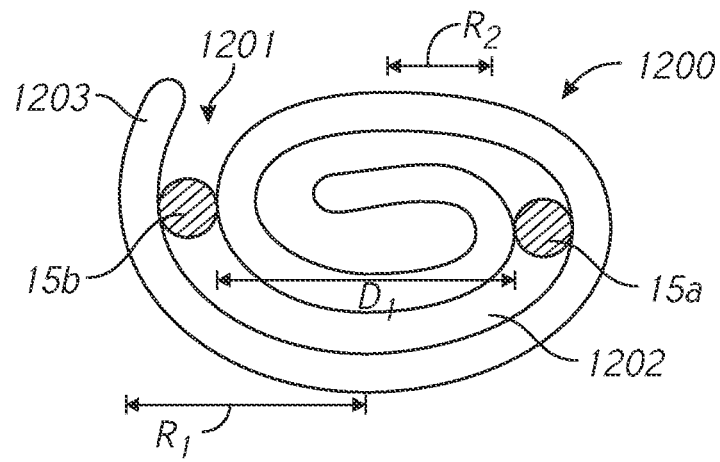
FIGS. 12 and 13 are top views of a spiral papillary muscle adjustment device in accordance with one or more embodiments.
Figure 13:
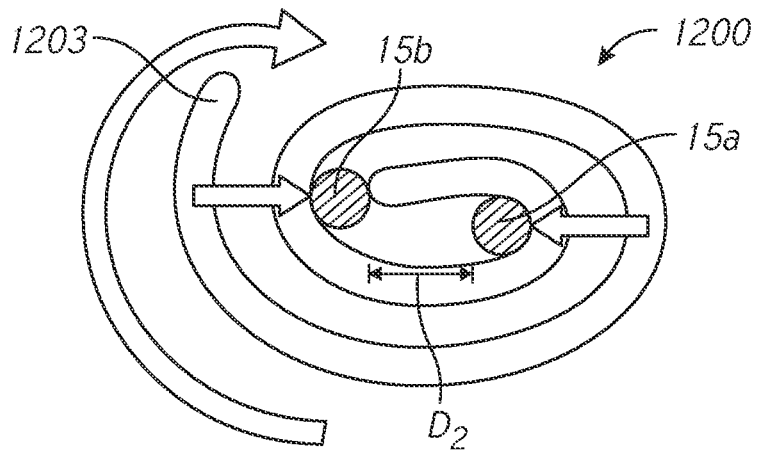

FIG. 11 illustrates a papillary muscle and/or ventricular adjustment device 1100 that may be at least partially wrapped around one or more papillary muscles of the ventricle 3 of a heart to thereby draw such papillary muscles towards one another to provide valve correction, as described in detail herein. In certain embodiments, the papillary muscle approximation device 1100 comprises a cloth-covered memory metal ring or hoop that is configured to be implanted at or near the base of the papillary muscles. Once both papillary muscles (or possibly 3 papillary muscles for right ventricular applications) are captured by the device 1100, in some embodiments, the shape and/or configuration of the device 1100 may allow for the progressive approximation of the papillary muscles through rotation or other type of manipulation of the device 1100. For example, FIGS. 12 and 13 illustrate top-down views of an example embodiment of a spiral papillary muscle approximation device, which may represent an embodiment of the hoop-type device shown in FIG. 11. As shown in FIG. 12, a spiral papillary muscle approximation device 1200 may comprise a maze-type design, wherein a radius R1 of the device at or near a first end 1203 of the device is greater than the radius R2 at or near a midpoint of the spiral form. The hoop or spiral device 1100 of FIG. 11 is shown as deployed in the left ventricle 3 of a heart, wherein the hoop/spiral 1100 has captured both papillary muscles 15*a*, 15*b*, therein. With reference to FIG. 12, the top-down view of FIG. 12 shows a spiral implant device 1200 having captured therein first and second papillary muscles 15*a*, 15*b* within the windings of the spiral 1200. For example, the opening 1201 of the spiral device 1200 may be passed around the papillary muscles, wherein the spiral device 1200 may be rotated (clockwise with respect to the particular orientation and configuration shown in FIG. 12, although other embodiments may provide for counter-clockwise rotation) to bring the papillary muscles further within the void 1202 between the spiral windings, and therefore closer together. The rotated device 1200 and approximated papillary muscles trapped there are shown in FIG. 13.

Although shown with a partially elliptical shape or form, it should be understood that the spiral device 1200 may have a circular or other shape or form. The end portion 1203 and/or opening 1201 may be used to engage papillary muscles from behind. Although certain embodiments are described herein in the context of papillary muscle trapping or engagement by a spiral device, it should be understood that other types of anatomy of the ventricle may be trapped within a spiral device in some implementations, such as trabeculae. The spiral/hoop devices shown in FIGS. 11 and 12 may have any suitable or desirable thickness. In some implementations, such devices comprise temperature-activated shape memory material. Furthermore, in some implementations, the spiral device 1200 may be implanted using a guide wire, which may initially be wound around the papillary muscles or other anatomy, wherein the spiral device 1200 is configured to be passed over or follow the guide wire in order to assume the deployed position around one or more papillary muscles. As shown in FIG. 13, by winding the spiral device 1200, the papillary muscles may move from an initial distance D1 to a restrained distance D2 by winding the spiral device 1200. The spiral device 1200 may first capture a first papillary muscle 15*a*, wherein subsequent rotation of the device 1200 may allow for capturing of the second papillary muscle 15*b* as well. Subsequent rotating of the device 1200 may provide inward approximation of the papillary muscles.

Figure 14:
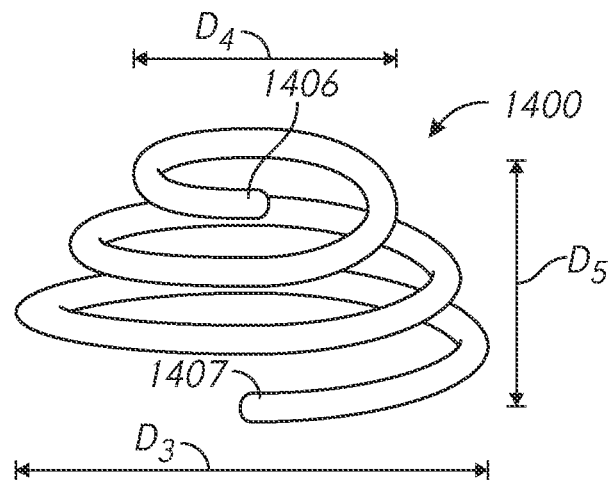
FIG. 14 is a perspective view of a tapered spiral papillary muscle adjustment device in accordance with one or more embodiments.

FIG. 14 shows a perspective side view of an embodiment of a spiral papillary muscle approximation device 1400 having an at least partially tapered, spring-type shape, wherein the spiral device 1400 has a greater diameter D3 associated with a first end 1407 of the device, and a second, smaller diameter D4 associated with a second end 1406 of the device 1400, wherein the first end 1407 and the second end 1406 are vertically offset by a distance D5 to create the tapered shape shown. The papillary muscle approximation devices of FIGS. 11-14 may advantageously incorporate one or more of the following features: a cloth covering, a maze-type design that is such as to draw captured papillary muscles together when rotated, and/or a tapered, spring-type shape, as shown in FIG. 14. Any of the devices shown in FIGS. 11 through 14 may be delivered to the ventricle of a heart through a percutaneous trans-catheter procedure and may be implanted without requiring cardiac bypass in certain implementations.

Additional Embodiments

Depending on the embodiment, certain acts, events, or functions of any of the processes described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

What is claimed is:

1. A method for treating a heart valve, the method comprising:
   introducing a coil to a ventricle of a heart;
   wrapping the coil along an inner wall of the ventricle; and
   capturing papillary muscles of the ventricle within the coil to thereby draw the papillary muscles together.

2. The method of claim 1, wherein the coil comprises an outer sleeve, and a spring element disposed at least partially within the outer sleeve.

3. The method of claim 2, wherein the outer sleeve comprises one or more tissue anchor features.

4. The method of claim 2, wherein the outer sleeve comprises material that promotes ingrowth with tissue of the inner wall of the ventricle.

5. The method of claim 2, wherein the spring element is configured to slide within the outer sleeve to accommodate contraction and expansion of the ventricle.

6. The method of claim 2, further comprising securing one or more of the outer sleeve and the spring element to an apex region of the ventricle.

7. The method of claim 2, wherein the spring element is fixed to the outer sleeve at one or more locations.

8. The method of claim 1, further comprising securing the coil in an expanded state using one or more biodegradable elements, and allowing the one or more biodegradable elements to degrade to thereby cause the coil to assume a contracted state.

9. A method for treating a heart valve, the method comprising:
   introducing a helical cinching device to a ventricle of a heart using a transcatheter access path, the helical cinching device having a spring bias;
   wrapping the helical cinching device along an inner wall of the ventricle; and
   drawing inward, using the spring bias of the helical cinching device, at least one of the inner wall of the ventricle or papillary muscles captured by the helical cinching device to thereby remodel a heart valve associated with the ventricle to reduce regurgitation.

10. The method of claim 9, wherein the helical cinching device has a dual-layer form including:
    an outer sleeve layer; and
    an inner spring disposed at least partially within the outer sleeve layer.

11. The method of claim 10, wherein the inner spring comprises memory metal.

12. The method of claim 10, wherein the inner spring is free to axially slide within the outer sleeve layer.

13. The method of claim 9, wherein said wrapping the helical cinching device involves wrapping the helical cinching device behind trabeculae carneae.

14. The method of claim 9, further comprising anchoring the helical cinching device to the inner wall of the ventricle using tissue anchoring barbs of the helical cinching device.

15. The method of claim 9, further comprising anchoring a distal end of the helical cinching device to an apex region of the ventricle.

16. The method of claim 9, further comprising suturing the helical cinching device to the inner wall of the ventricle.

17. The method of claim 16, wherein suture used in said suturing the helical cinching device to the inner wall of the ventricle is biodegradable.

18. A method for treating a heart valve, the method comprising:
    introducing an elongate sleeve to a ventricle of a heart;
    attaching the elongate sleeve to an inner wall of the ventricle;
    introducing a coil spring to the ventricle;
    after said attaching the elongate sleeve to the inner wall of the ventricle, inserting the coil spring in the elongate sleeve inside the ventricle; and
    drawing the inner wall of the ventricle inward using the coil spring and the elongate sleeve, thereby bringing leaflets of an atrioventricular heart valve into coaptation to reduce regurgitation associated with the heart valve.

19. The method of claim 18, wherein said attaching the elongate sleeve to the inner wall involves suturing the elongate sleeve to the inner wall.

* * * * *